US008562562B2

(12) United States Patent
Walter et al.

(10) Patent No.: US 8,562,562 B2
(45) Date of Patent: Oct. 22, 2013

(54) INTRAVENOUS FLUID HEATER

(75) Inventors: Joanne S. Walter, Blue Ridge, GA (US); Darrel Saunders, Simpsonville, SC (US); Craig B. Berky, Milford, OH (US); Kurt Klingenberg, Cold Spring, KY (US)

(73) Assignee: North American Rescue, LLC, Greer, SC (US)

( * ) Notice: Subject to any disclaimer, the term of this patent is extended or adjusted under 35 U.S.C. 154(b) by 193 days.

(21) Appl. No.: 13/209,387

(22) Filed: Aug. 13, 2011

(65) Prior Publication Data

US 2013/0041317 A1 Feb. 14, 2013

(51) Int. Cl.
*A61F 7/12* (2006.01)
(52) U.S. Cl.
USPC .............................. 604/114; 604/113; 607/104
(58) Field of Classification Search
USPC ........... 604/113, 114; 607/104, 106; 392/478, 392/479
See application file for complete search history.

(56) References Cited

U.S. PATENT DOCUMENTS 5,125,069 A * 6/1992 O'Boyle ....................... 392/465
6,142,974 A * 11/2000 Kistner et al. ................ 604/113

* cited by examiner

*Primary Examiner* — Laura Bouchelle
(74) *Attorney, Agent, or Firm* — McNair Law Firm, P.A.; Douglas W. Kim (57) ABSTRACT

This invention is directed to a portable intravenous fluid heater that can weight less than 10 oz having an internal power supply internal tubing that is heated by a heating element; a logic assembly; an external power terminal for connecting an external power supply; and computer readable instructions, that when executed by the processor, perform the steps of receiving output temperature from the fluid output heat sensor, removing power from the heating element if the output temperature is above a predetermined temperature to reduce the temperature of fluid exiting the tubing and delivering power to the heating element when the output temperature is below a predetermined temperature.

41 Claims, 8 Drawing Sheets

Fig 12

INTRAVENOUS FLUID HEATER

FIELD OF THE INVENTION

The present invention relates to an intravenous fluid warmer and, in particular, relates to an intravenous fluid warmer that is particularly suitable for use in warming fluids and the management of hypothermia in combat and other extreme weather and/or remote environments and locations.

BACKGROUND OF THE INVENTION

Based upon studies preformed by the United State military, the number one cause for preventable combat death is one or more extremity hemorrhage. In fact, extremity hemorrhage accounts for approximately 60% of studied preventable combat deaths. When an injured person hemorrhages, hypothermia prevention and management is of critical importance. Hypothermia can lead to cardiac arrhythmias, decreased cardiac output, increased systemic vascular resistance, and most importantly, induced coagulopathy by inhibition of the clotting cascade. If hypothermia is not prevented in this casualty demographic the potential exists that the injured person will not be able to form a clot due to the disruption of the clotting cascade and may potentially bleed to death from an otherwise survivable wounding.

Many wounded personal are given intravenous fluid. Based upon the type of fluid provided, the fluid temperature can much colder than the body temperature and even below 40° F. (4.4° C.). Given that it is recommended that the fluid entering the injured person be at least 98.6° F. (37° C.), it would be advantageous to heat the IV fluid prior to is being delivered to the injured person.

IV fluid heaters or warmers have traditionally been powered by an AC power source because of the high power required to heat IV fluids. The temperature difference between the fluid and the optimal delivery temperature can be as much or even greater than 60° F. (15.5° C.). Battery powered IV fluid warmer have heretofore had poor performance because of the battery sources which have been available.

One known battery-powered blood or IV fluid warmer is marketed as the Thermal Angel® and is produced by Estill Medical Technologies, Inc. having an address of 4144 N. Central Expressway. Suite 260 Dallas, Tex. 75204 and was found on the website http://www.thermalangel.com. The TA-200 model Thermal Angel® device is disclosed as using a 12 volt, rechargeable, lead acid battery weighing 6.25 pounds. This battery requires an external charger and thus requires an extra piece of equipment for operational use. The TA-200 model Thermal Angel® battery has a heating capacity of about 2 to 4 liters of room temperature IV fluid or about 2 to 3 liters of blood. It is understood at this time that the TA-200 model Thermal Angel® battery cannot be charged while the fluid warmer is in use. Further, it is understood that the TA-200 model Thermal Angel® battery has a complete charge time of approximately twelve hours and cannot be fast charged. In addition, The TA-200 model Thermal Angel® battery has only a simplified gauge which is only accurate when the battery is not in use.

Another known battery-powered, IV fluid warmer relates to a lithium polymer (LiPo) battery because LiPo batteries were known to have extremely low internal impedance and to be particularly suitable for high current applications. For example, US Patent Application No. 2007/0105010 A1, to Cassidy, published May 10, 2007 and entitled Lithium Polymer Battery Powered Intravenous Fluid Warmer, discloses such a known LiPo as having a relatively high energy density, no exhibited memory effects, and to be environmentally safe. In particular, the US 2007/0105010 reference also discloses a battery management system for such an IV heater which addresses potential issues with LiPo batteries because they may become dangerous if overcharged or over-discharged and in such circumstances the batteries can explode or catch fire.

Other prior art techniques and devices exist for warming fluids to be infused intravenously into a body, such as a human or other animal. One such conventional device is disclosed in U.S. Pat. No. 5,245,693 ("the '693 patent"). The '693 patent is directed to an intravenous fluid heater that includes a disposable cassette containing a heat exchanger. The preferred embodiment of the heat exchanger disclosed in the '693 patent includes a passageway-defining inner layer sandwiched between a pair of flexible, metal foil membranes. The inner layer defines an extended, e.g., serpentine, path for fluid to be warmed, and serves to space apart and insulate the metal foil membranes from one another. Inlet and outlet ports to the serpentine fluid path are defined in one of the two foil membranes. Heat generated by heating elements which sandwich the heat exchanger is transferred through the metal foil membranes to the fluid flowing through the serpentine path. The heating elements are designed to be graduated, that is, to generate more heat in the area of the inlet portion of the serpentine path than in the area of its outlet.

A yet further disadvantage of the heating arrangement disclosed in the '693 patent is that although means are included for reducing gas bubble formation in the infusion fluid, no means are provided for automatically determining whether such bubbles are present in the fluid or whether there has been reduction in fluid flow rate, and for taking appropriate action (e.g., providing warning and/or stopping fluid flow into the patient) in the event such conditions are determined to be present. As will be appreciated by those skilled in the art, if left unchecked these types of conditions can be, at minimum, deleterious to patient well-being, and at most, life-threatening.

Another conventional infusion fluid warming device is disclosed in U.S. Pat. No. 5,254,094 ("the '094 patent"). In the arrangement disclosed in the '094 patent, a box which may be attached to a patient's arm is provided. Two chambers are included in the box, containing a heat exchanger element constructed from a continuous length of stainless steel tubing in the form of two parallel coils which are connected to each other by a straight length of tubing. The box includes a passage between the chambers such that a warming fluid may be introduced through an aperture in the box into one of the chambers, flow into the other chamber, and then exit the warmer through another aperture in the box. The infusion fluid to be warmed is supplied to the coils through a first flexible plastic inlet tube and discharged for infusion into a patient through a second flexible plastic tube. The warming fluid is supplied via fluid supply tubing to the box from a separate fluid source that is not dimensioned or suitable for being worn by the patient, such as a water heater. A temperature sensor located in the infusion fluid path between the box and the infusion sites may be provided for generating signals indicative of the temperature of the infusion fluid for provision to a microprocessor contained in the same unit comprising the water heater. The microprocessor also receives outputs from a water temperature sensor and controls the water heater, based upon the outputs from these sensors and a desired infusion fluid temperature set by the user, so as to maintain the heating water at a temperature for heating the infusion fluid to the desired temperature.

Disadvantageously, use of a warming fluid/infusion fluid type of heat exchanger, and a warming fluid heater that is remote from the heat exchanger and not wearable by the patient, make '094 patent's arrangement bulky, and relatively difficult to move and set up for use. Also disadvantageously, if even a single crack, pin-hole, imperfect seal, or other opening exists in the infusion fluid tubing/fittings in the heat exchanger, the infusion fluid may become contaminated with the warming fluid.

Other examples of infusion fluid warming prior art are disclosed in U.S. Pat. Nos. 5,381,510, 4,731,072, 3,443,060, 3,475,590, 3,485,245, 3,590,215, 3,614,385, 3,640,283, 3,853,479, 4,038,519, 4,108,146, 4,167,663, 4,293,762, 4,309,592, 4,938,279, 4,847,470, 4,574,876, 3,399,536, 4,962,761, 5,125,069, 4,908,014, 4,906,816, 4,844,074, 4,707,587, 4,759,749, 4,782,212, 4,801,777, 4,680,445, 4,678,460, 4,532,414, 4,464,563, 4,314,143, 4,356,383, and, 4,878,537.

While these and other known devices and technologies offer various advantages and benefits, they also suffer from the aforesaid and/or other disadvantages and drawbacks.

Accordingly, it is an object of the present invention to provide a portable intravenous fluid heater that is light weight with an internal power supply.

It is another object of the present invention to provide a portable intravenous fluid heater that is light weight with an internal power supply that can also use an external power supply.

It is an object of the present invention to provide a portable intravenous fluid heater that includes replaceable internal tubing and inter power supply.

SUMMARY OF THE INVENTION

The objects of the invention are accomplished by providing a portable intravenous fluid heater that can weight less than 10 oz comprising: a housing; an internal power supply contained within the housing; tubing having a tubing input connector external to the housing and a tubing output connector external to the housing; a logic assembly carried by the housing having a processor and computer readable instructions; a heating element connected to the logic assemble and adjacent to the tubing; an output fluid heat sensor connected to the logic assembly disposed adjacent to a tubing output connector attached to the tubing output end for sensing the temperature of fluid flowing out of the tubing; an external power terminal connected to the logic assembly for connecting an external power supply; a power supply selection switch included in the logic assembly for switching from the internal power supply to a connected external power supply when a external power supply is connected and delivering power; and, computer readable instructions, that when executed by the processor, perform the steps of receiving output temperature from the fluid output heat sensor, removing power from the heating element if the output temperature is above a predetermined temperature to reduce the temperature of fluid exiting the tubing and delivering power to the heating element when the output temperature is below a predetermined temperature.

DESCRIPTION OF THE DRAWINGS

The invention will be more readily understood from a reading of the following specification and by reference to the accompanying drawings forming a part thereof, wherein an example of the invention is shown and wherein.

DESCRIPTION OF A PREFERRED EMBODIMENT

Figures 1, 2:
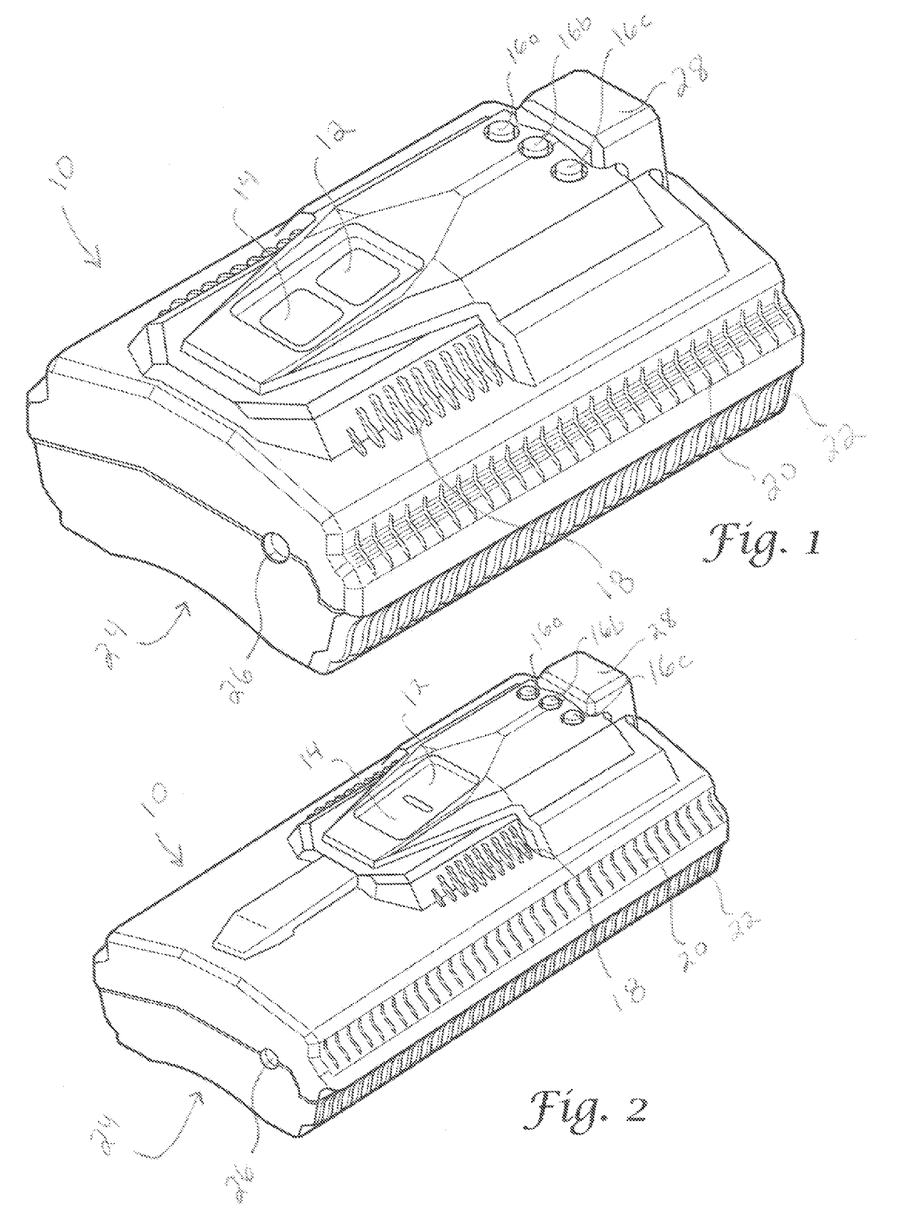
FIGS. 1, 2 and 3 is a perspective view of aspects of the invention.

Referring to FIGS. 1 and 2, housing 10 is shown having an on/off actuator 12 and power check actuator 14. Upper fins 18, mid-fins 20 and lower fins 22 can be included in the housing for providing structural strength to the housing and help cool the external surface of the housing.

Indicators 16a through 16c are disposed on the housing for indicating operational status of the unit. In one embodiment, indicator 16a is a red light that is actuated, in one case illuminated with different colors, according to the operational status. In one alternative embodiment, the indicator could include an audible indicator. Operational status includes when the unit is operating within parameters, when the current delivered to the unit to too great, when the voltage delivered to the unit is too great, when the logic assembly reaches too high a temperature, when the internal power supply drops below a predetermined level such as 25% of its capacity, when intravenous fluid flowing out of the unit has a temperature of 90° F. of lower, when intravenous fluid flowing out of the unit has a temperature higher than 104° F. and other operational conditions. In one embodiment, indicator 16b is a yellow light that can represent when the fluid flowing out of the unit has a temperature between 70° F. and 90° F. In one embodiment, indicator 16c is a green light that can represent when the fluid flowing out of the unit has a temperature above 90° F., that the internal power supply is has 75% of its capacity remaining, that the external power supply is delivering sufficient power or other normal operational conditions.

A receiving area 24 is defined in said housing for receiving the arm or leg of an injured person so that the housing can be placed on the arm or leg and better secured from rotating or being removed from the arm or leg. The receiving area can also be used to attach the housing to a litter, vehicle or other transportation means for moving the injured person. Therefore, the unit can be transported securely with the injured person without having to separate the unit from the injured person. An output opening 26 is defined in the housing as well as an input opening in the housing for receiving fluid output connectors and fluid input connectors, respectively. An external power supply opening is defined in portion 28 of the housing so that an external power supply terminal can be accessed external to the housing.

Figure 3:
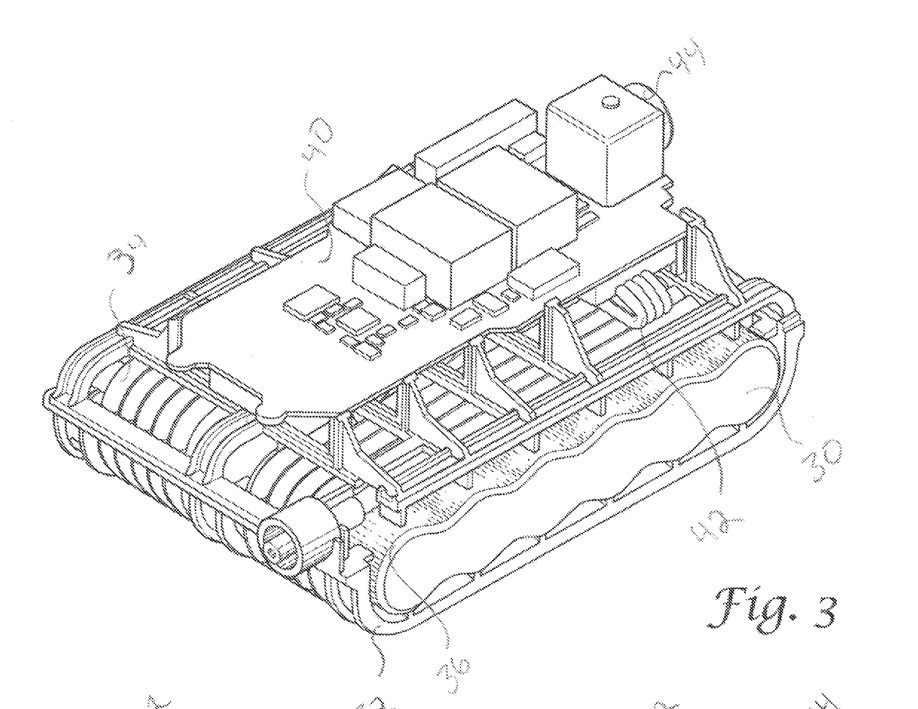
Figure 4:
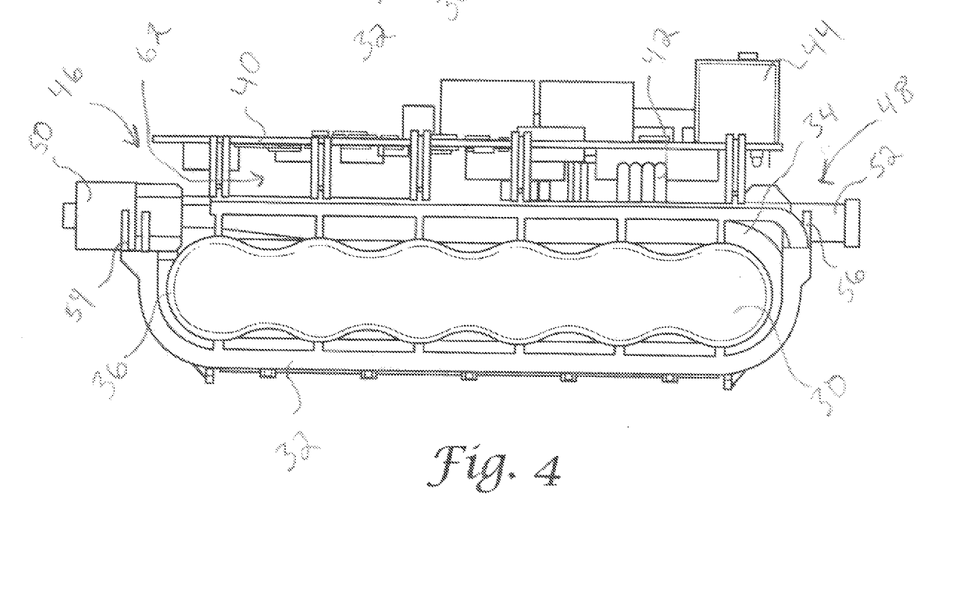
FIG. 4 is a side view of aspects of the invention.

Referring to FIGS. 3 and 4, components of the invention are shown in further detail. An internal power supply 30 is carried by a chassis 32. In one embodiment, the internal power supply is a DC power supply comprising a series of batteries contained in a wrapping 36. Tubing 34 is wrapped around the internal power supply so that heat generated from the internal power supply can be transferred to the fluid in the tubing to provide auxiliary heat to the intravenous fluid flowing in the tubing. The tubing is wrapped several times to provide sufficient surface area across the tubing for sufficiently heating the intravenous fluid to a predetermined temperature; 104° F. in one embodiment, the recommended temperature for intravenous fluid delivery.

A logic assembly 40 can be attached to the housing or chassis and include a processor, computer readable storage medium and computer readable instructions stored on the computer readable storage medium. The logic assembly provides for some of the functionality of this invention. The logic assembly is electronically connected through connections 42 to the internal power source and heating element.

An external power supply terminal 44 is included in the logic assembly. The terminal can be a BA-5590 connection or other connection. The external power supply can include DC or AC power sources as an AC/DC converter is included in the logic assembly. External power supplies can include external batteries, BA-5590, AC adaptors for connecting the logic assembly to an AC power source such as a vehicle's electrical system, generators, or the like so that power of multiple types can be used to deliver heated intravenous fluid to an injured person for much longer intervals than can be provided by the internal power supply alone. In one embodiment, the computer readable instructions include instructions which limit the operational time of the unit to a predetermined time such as 72 hours in one embodiment.

The tubing can include an output end 46 and an input end 48. Fluid output connector 50 can be attached to the output end and fluid input connector 52 can be attached to the input end. Since external IV tubes at attached to the fluid output and fluid input connectors, output connector stop 54 and input connector stop 56 can be included in the chassis or carried by the housing. These connector stops secure the output connector and the input connector so that a portion of the connector is secured externally to the housing allowing tubes to be connected to them and a portion of the connectors is secured internally to the housing so that they do not pull away from tubing 34.

An input fluid heat sensor can be connected to the logic assembly and disposed at the input end of the tubing to measure the temperature of fluid entering the tubing. An output fluid heat sensor 64 (FIG. 6) can be connected to the logic assembly and disposed at the output end of the tubing to measure the temperature of fluid exiting the tubing. A fluid flow sensor 62 (FIG. 6) can be connected to the logic assembly and disposed inside the tubing for measuring the flow rate of fluid flowing in the tubing. A voltage sensor can be included in the logic assembly for sensing the voltage applied to the logic assembly and the electrical circuit defined by the logic assembly, power source (intern or external) and the heating element. The logic assembly can include a logic assembly temperature sensor which measures the temperature of the logic assembly.

Figure 5:
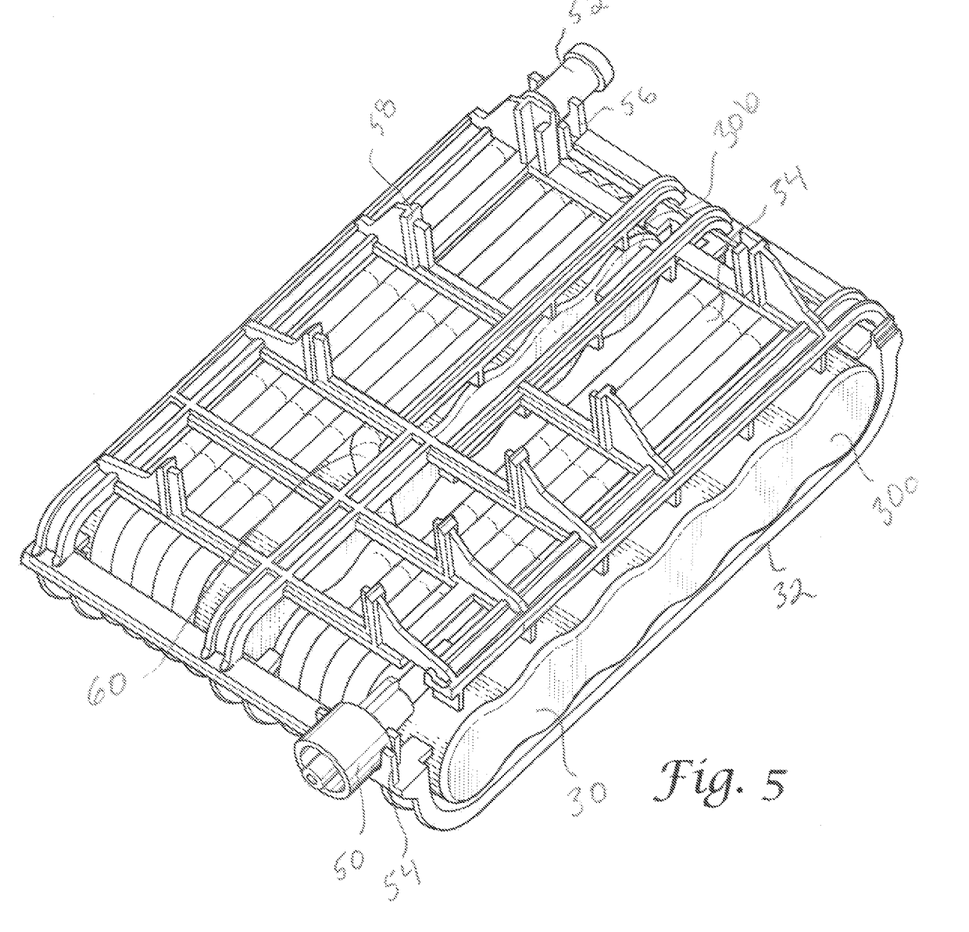
FIG. 5 is a perspective view of aspects of the invention.
Figure 6:
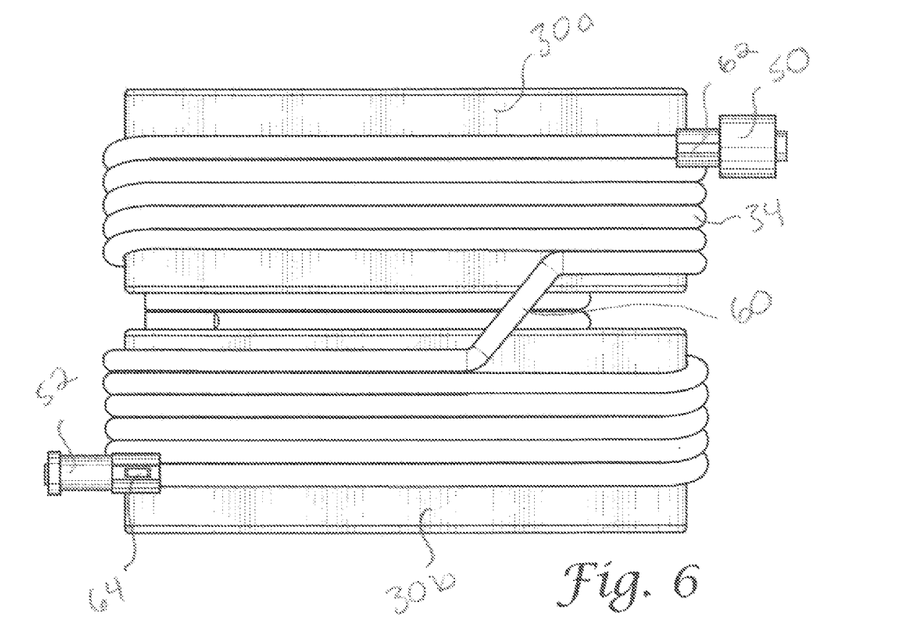
FIG. 6 is a top view of aspects of the invention.

Referring to FIGS. 5 and 6, logic assembly stands, such as 58, are used to separate the logic assembly from the tubing and the intern power supply so that the logic assembly does not overheat from heat radiating from the tubing or from the internal power supply. A cooling space 63 (FIG. 4) is defined between the logic assembly and the tubing allowing air to circulate around the logic assembly through convection resulting in a cooling of the logic assembly.

In one embodiment, the tubing, inter power supply and logic assembly are carried by the housing without a separate chassis. In one embodiment, the chassis is attached to the housing. In one embodiment, the logic assembly is connected to a first intern power supply 30a and a second internal power supply 30b. These two power supplies can be connected in parallel so that any fault with one internal power supply would still allow the logic assembly and heating element to be power by the other internal power supply. The tubing can have a portion wrapped around the first internal power supply and with a transition portion 60 of the tubing, have a portion wrapped around the second internal power supply. In this arrangement, the heat generated from both power supplies can be used to supplement the heat applied to the tubing from the heating element.

In one embodiment the internal power supply is rechargeable such as with lithium batteries which can be recharged when the logic assembly determine there is sufficient power from an external power supply to recharge the inter power supply.

Figure 7:
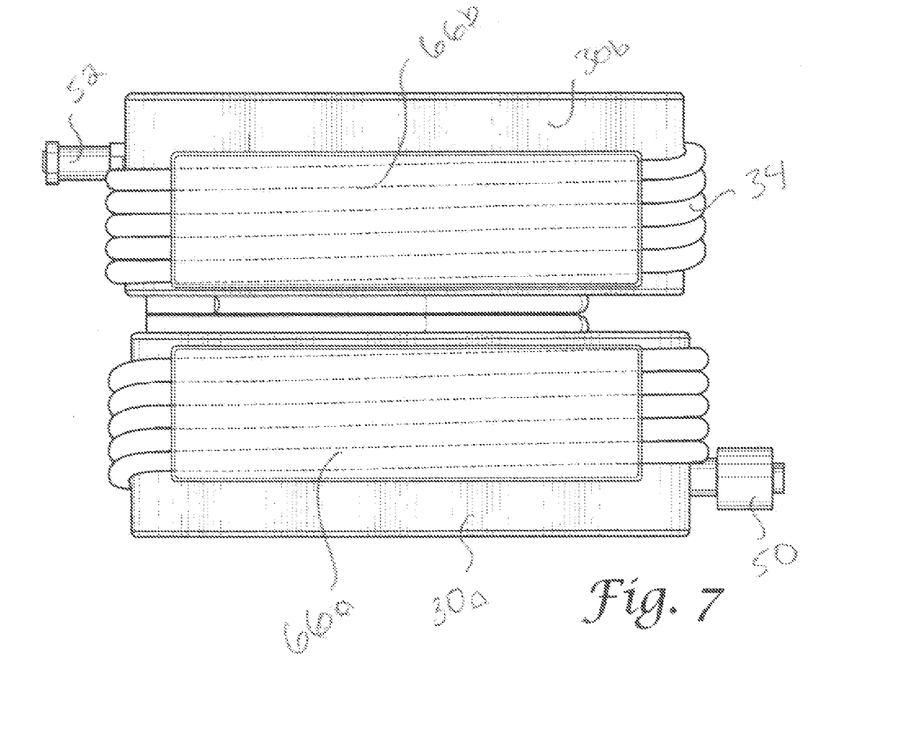
FIG. 7 is a bottom view of aspects of the invention.

Referring to FIG. 7, a dissipation plate can be included and carried by the housing to more uniformly distribute heat generated from the heating element to the tubing. In one embodiment, dissipation plate 66a is disposed adjacent a portion of the tubing and dissipation plate 66b is disposed adjacent another portion of the tubing. Through the heating element heating the dissipation plate, the dissipation plate can more uniformly distribution heat across a larger surface area of the tubing.

Figure 8:
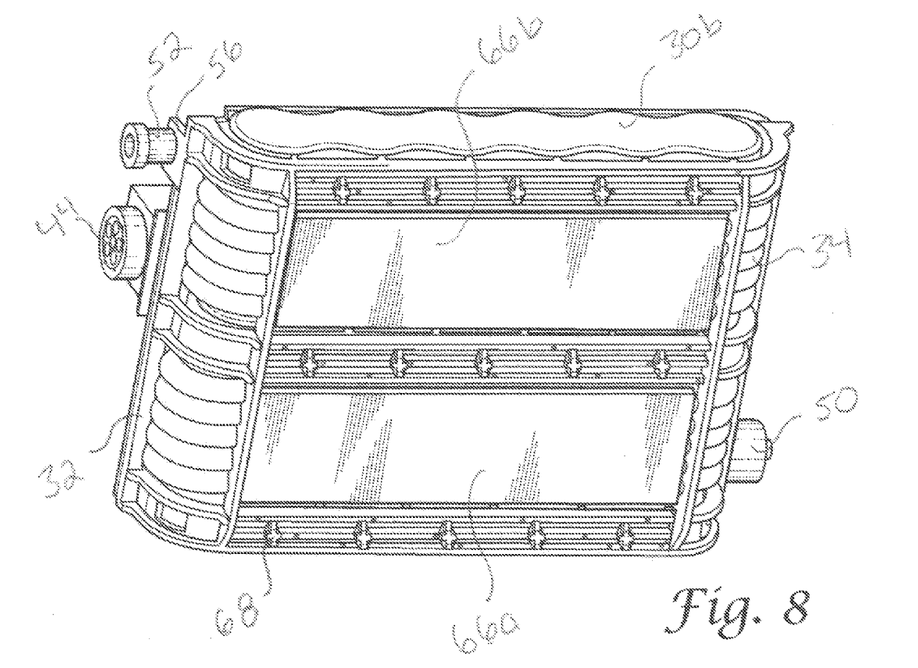
FIGS. 8, 9 and 10 are bottom perspective views of aspects of the invention.
Figure 9:
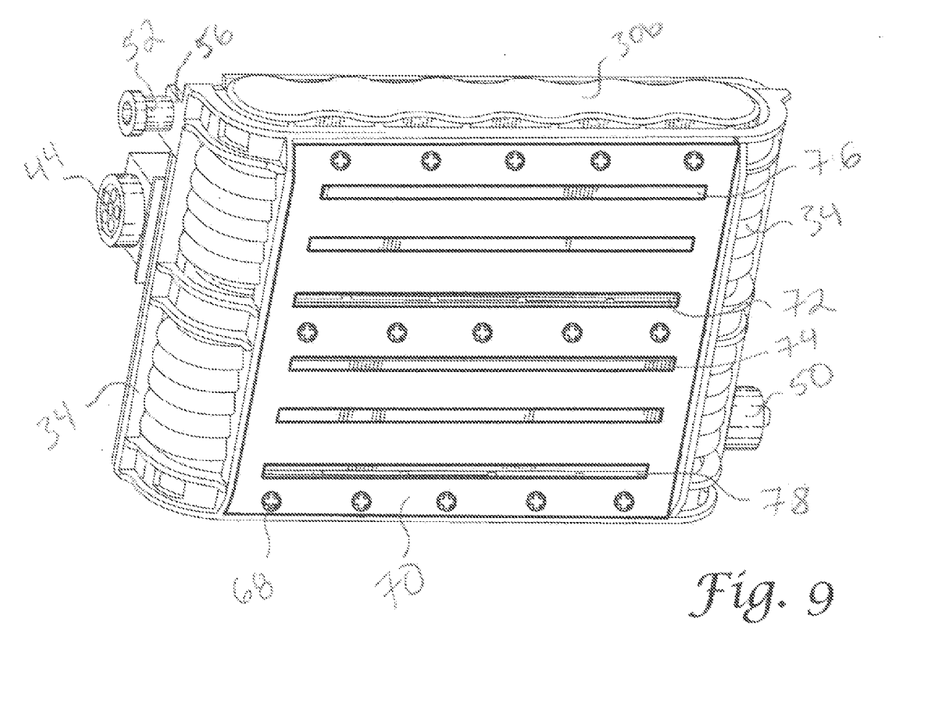
Figure 10:
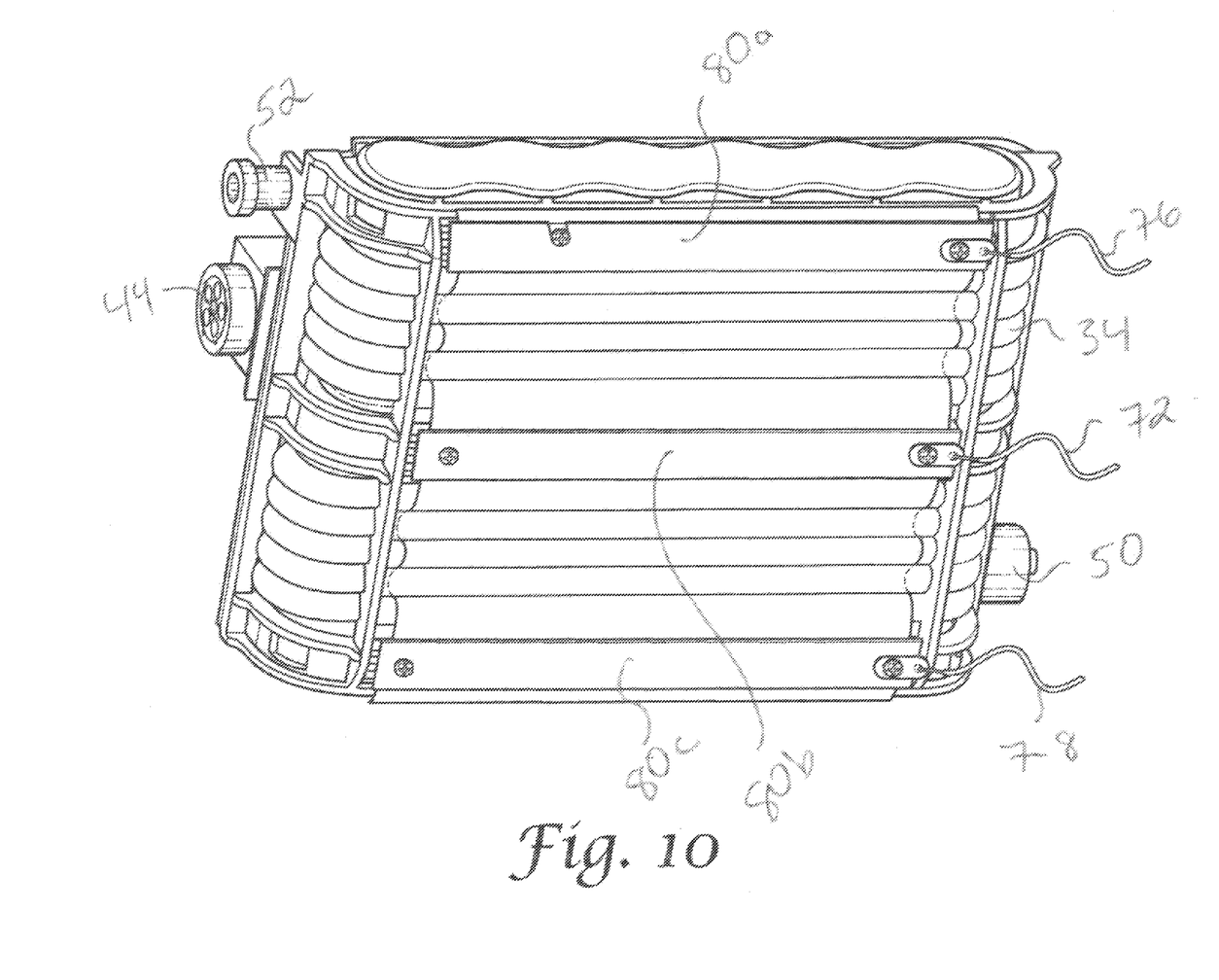

Referring to FIGS. 8 and 9, the chassis or housing can include heating element mounting members such as 68. These mounting members are used to secure a thin film heating element to the chassis or housing. The heating element can include positive terminals 72 and 74 and negative terminals 76 and 78. When power is supplied to these terminals the heating element generates heat. There can in a single heating element or a plurality of heating elements arranged in series or parallel. The heating element can be adjacent the tubing, adjacent to dissipation plates or interwoven with the tubing as shown in FIG. 10. Securing panels 80a through 80c can be used to secure the heating element to the chassis or the housing.

External power supply terminal 44 is attached to the logic assembly.

In one embodiment, the chassis, attached to the tubing and intern power supply can be removed form the housing and replaced. In this embodiment, the logical assembly is removable connected to the heating element. In one embodiment, the logic assembly can be removed from the housing and replaced. In this embodiment, a wiring harness can be used to allow the logic assemble to be removable connected to other components such as the various sensors and the heating element.

Figure 11A:
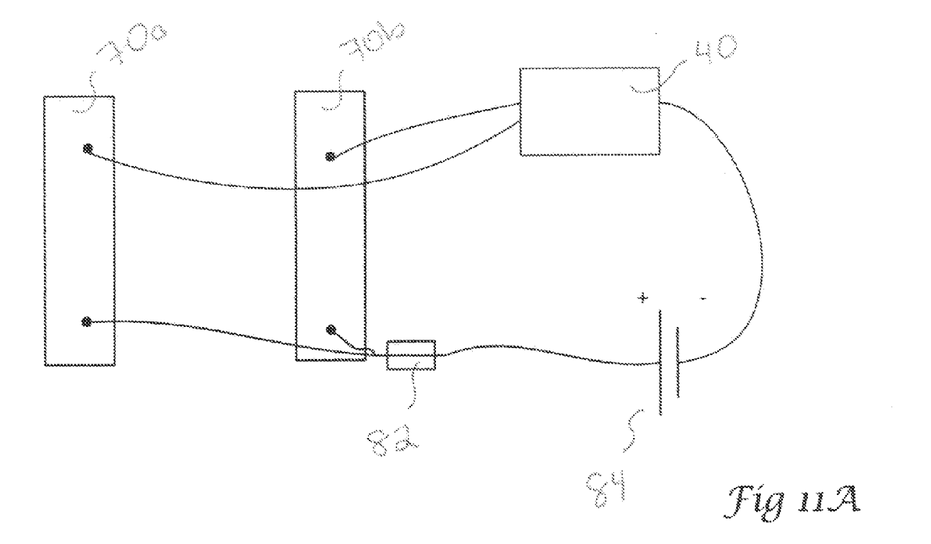
FIGS. 11A and 11B are schematics of aspects of the invention.
Figure 11B:
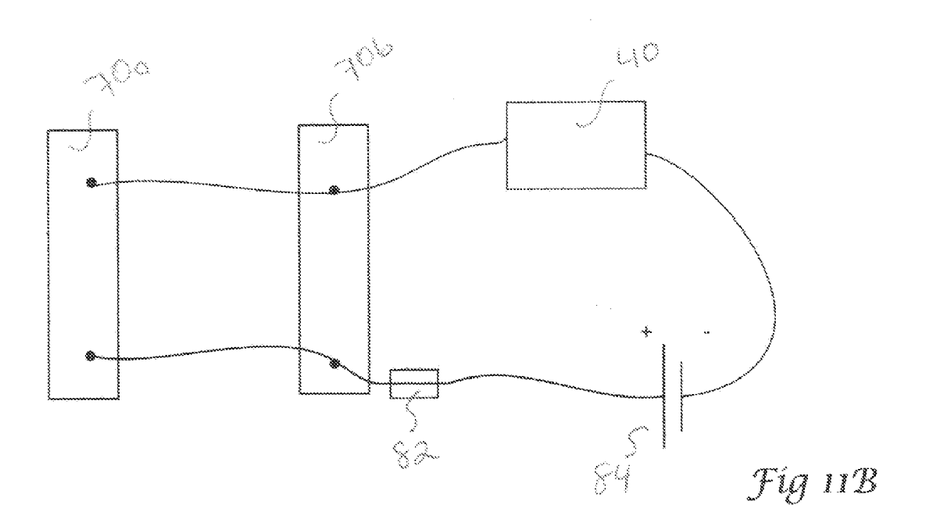

Referring to FIG. 11A an electrical circuit defined by heating elements arranged in parallel 70a and 70b are shown connected to logic assembly 40, power supply (intern or external) 84 and a circuit breaker 82. If the event that the temperature of the circuit is too great, the circuit breaker can "trip" or "blow" and the electrical current is open ceasing the deliver of power to the heating elements. The circuit breaker can be a fuse, switch, thermostat or the like which open if a predetermined temperature is exceeded. FIG. 11B shown the heating elements arranged in series.

In one particular embodiment, the heating element is a thin-film consisting of a relatively thin polyamide, or polyester film impregnated with a resistive carbon layer onto which conductive busses (leads) are printed. The leads can be comprised of low resistance, highly conductive materials such as silver, copper or gold. The film of the heater element itself is less than 0.5 mm thick with strength, flexibility and reliability. In one particular embodiment the heater is laminated with a 0.1 mm layer of Teflon™ to allow for forming heater into a wave pattern. Critically, this heater technology draws far less power than competitive alternatives allowing for extended battery life and lightweight, highly portable designs. In one exemplary embodiment, the heater material of the heater elements may be directly applied to the housing members using a spray and/or deposition technique. In one alternate embodiment, it is possible to use a single layer carbon-based resistive film that is directly applied to the outer surface of the inner housing.

Figure 12:
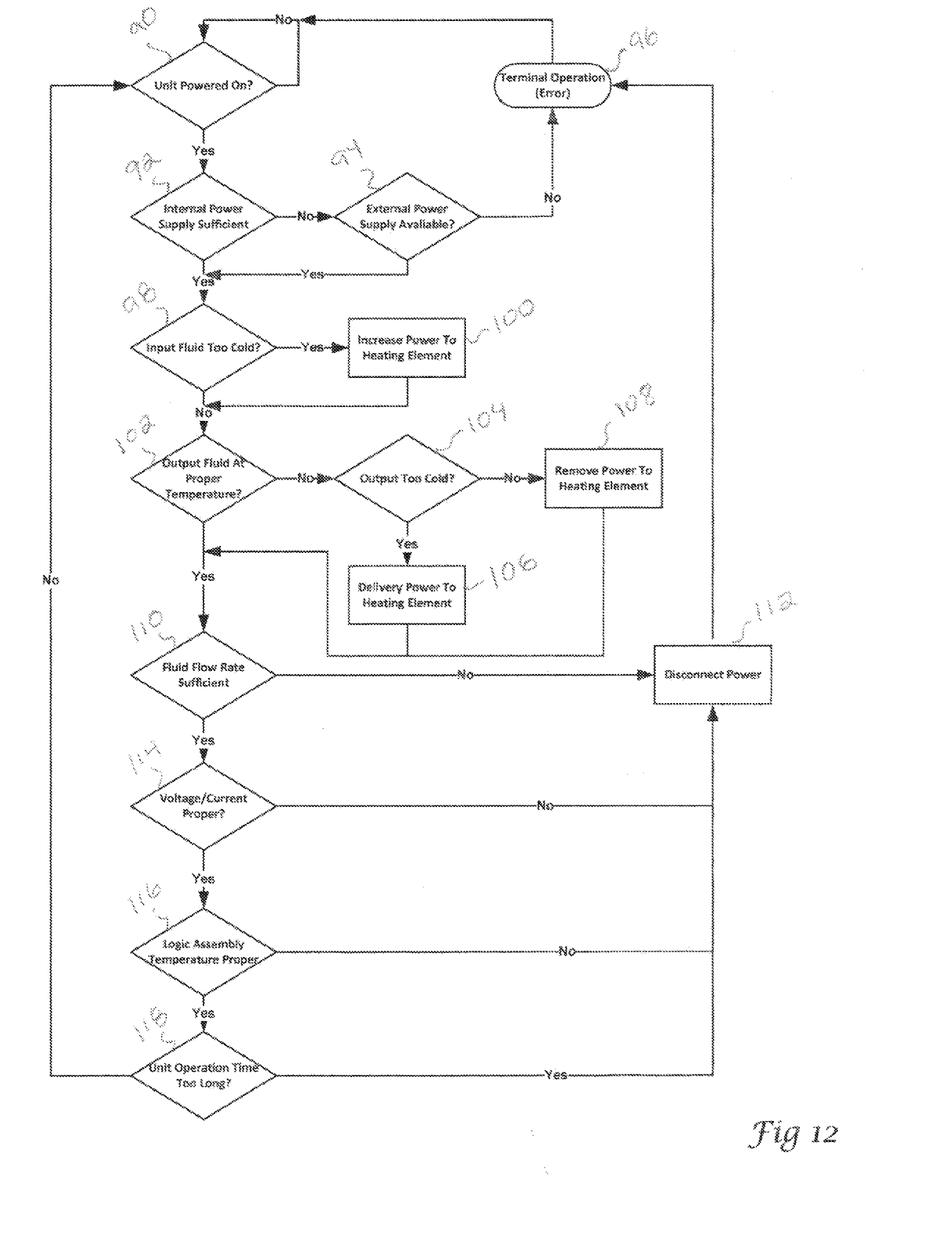
FIG. 12 is a flowchart illustrating aspects of the invention.

Referring to FIG. 12, the computer readable instructions that when executed by the processor included in the logic assembly, perform the following steps. First a determination is made at 90 whether the unit is powered on. The unit can be powered on through the power actuator located on the housing. If there is no power, the process returns to step 90. If there is power, a determination is made at 92 whether there is sufficient power being delivered by the internal power supply. In one embodiment, when the internal power supply drops below 25% of its capacity or has only 25% of its operational time remaining, the indicator can inform the use of the operation status, but the unit will continue to operate until the internal power supply is exhausted. If there is not sufficient power being delivered by the intern power supply, a determination at 94 is made whether there is an external power supply delivering sufficient power available. If not, the process ends at 96. If sufficient power remains, the indicator can inform the user of the operational status of the unit. External power can be a DC or AC source.

If sufficient power is available (internally or externally), a determination at 98 is made as to whether the intravenous fluid flowing into the tubing is below a predetermined temperature; 50° F. in one embodiment, 40° F. in another embodiment. In the event that the fluid entering the tubing is lower than the predetermined temperature, the power delivered to the heating element is increased at 100 to generate additional heat so that the temperature of the intravenous fluid exiting the tubing is approximately 104° F., the preferred exiting temperature. A determination is made at 102 to determine if the output temperature is at the proper temperature; preferably 104° F. in one embodiment. If the output temperature is not proper, as determination is made a 104 to see if the output temperature is too cold. If the temperature so too cold, power is delivered to the heating element at 106. When delivering power, the computer readable instructions can determine a duty cycle based on the difference between the actual output temperature and the desired output temperature. Other factors that can be included in the determination of the duty cycle is ambient temperature taken from a thermometer included in the logic assembly, flow rate and input temperature. For example, of the temperature of the intravenous fluid entering the unit is 50° F. the fluid would need to be raised 54° F. to reach an optimal output temperature. The duty cycle may be 90%. If the input temperature is 90° F., the duty cycle may be 5%.

The analog power supply is controlled by the digital logic assembly to reduce power consumption. The logic assembly uses high-resolution counters to modulate the duty cycle of a square wave. The power supplied to the heating element is digital because, at any given instant of time, the full DC supply is either fully on or fully off. The voltage or current source is supplied to the heating element by repeating a series of on and off pulses. The on-time is the time during which the DC supply is applied to the heating element, and the off-time is the period during which the power is switched off. The modulation rate, in one embodiment, is 300 times a second.

If the temperature is not too cold, it is too hot and power is removed from the heating elements allowing the fluid in the tubing to cool at 108.

A determination at 110 is made to see if the fluid rate is proper. If there is a clog, kink, obstruction, exhausted fluid source or other reason fluid is not properly flowing through the tubing, power is removed from the heater at 112 and the unit terminates at 96. The indicator can be actuated so that the use is informed of the improper fluid flow. The indicated can also include a audio indicator for errors such as improper fluid flow, temperatures errors and the like.

The voltage and current delivered to the logic assembly is determined to be proper at 114. If there is an error or improper voltage or current flow outside predetermined tolerances, the unit removes power form the hearing element at 114 and terminates a 96. The temperature of the logic assembly is determined to be proper at 116 and if it is outside predetermined tolerances, the unit removes power form the heating element at 114 and terminates a 96.

A clock included with the logic assembly tracks the elapse time that the unit is operating. In the event that the unit has been operating past a predetermined time, 72 hours in one embodiment, the unit removes power form the heating element at 114 and terminates a 96.

While a preferred embodiment of the invention has been described using specific terms, such description is for illustrative purposes only, and it is to be understood that changes and variations may be made without departing from the spirit or scope of the following claims.

What is claimed is:

1. A portable intravenous fluid heater comprising:
   a housing defining an internal cavity;
   an internal power supply contained within said internal cavity;
   tubing surrounding said internal power supply disposed in said internal cavity so that fluid flowing through said tubing receives auxiliary heat from said power supply, said tubing having an input end and an output end;
   a logic assembly carried by said housing having a processor and non-transitory computer instruction storage media and connected to said inter power supply;
   a heating element connected to said logic assemble;
   an input fluid heat sensor connected to said logic assembly disposed adjacent to a tubing input connector attached to said tubing input end for sensing the temperature of fluid flowing into said tubing;
   an output fluid heat sensor connected to said logic assembly disposed adjacent to a tubing output connector attached to said tubing output end for sensing the temperature of fluid flowing out of said tubing;
   a fluid flow sensor connected to said logic assembly and disposed inside said tubing for sensing the flow rate of fluid flowing in said tubing;
   an indicator attached to said logic assembly viewable externally to said housing for indication operational status;
   an external battery terminal connected to said logic assembly for connecting an external battery;
   a power supply selection switch included in said logic assembly for switching from said internal power supply to a connected external power supply when the external power supply is connected;
   a set of computer readable instructions embodied in said computer instruction storage media for:
   receiving an output temperature from said fluid output heat sensor, removing power from said heating element if said output temperature is above a predetermined temperature to reduce the temperature of fluid exiting said tubing and delivering power to said heating element when said output temperature is below a predetermined temperature,
   receiving an input temperature from said input fluid heat sensor, increasing power delivered to said heating element if said input temperature is below a predetermined temperature to heat fluid entering said tubing, receiving power level information from said internal power supply, actuating said indicator when said power level of said internal power supply drops below a predetermined level, receiving fluid flow rate information from said fluid flow sensor, actuating said indicator light when said flow rate is said tubing drops below a predetermined rate, and, receiving timing information from an internal clock included in said logic assembly representing elapse time said heater has been powered, discontinuing power to said heating element after a predetermined period of time has elapsed.

2. The apparatus of claim 1 including:
a logic assembly heat sensor connected to said logic assembly for sensing the temperature of said logic assembly; and,
said set of computer readable instructions include instructions for receiving temperature information from said logic assembly heat sensor, turning off power to said logic assembly if said output temperature information from said logic assembly is above a predetermined temperature.

3. The apparatus of claim 1 including:
a voltage sensor connected to said logic assembly for sensing the voltage connected to said logic assembly; and,
said set of computer readable instructions include instructions for receiving voltage information from said voltage sensor, turning off power to said logic assembly if said voltage from said logic assembly is above a predetermined value.

4. The apparatus of claim 1 wherein said set of computer readable instructions include instructions for controlling power delivered to said logic assembly through pulse width modulation.

5. The apparatus of claim 4 wherein said modulation rate of said pulse width modulation is 300 times per second.

6. The apparatus of claim 1 wherein said computer readable instructions for actuating said indicator when said power level of said internal power supply drops below a predetermined level actuates when said power level drops below 25% if its capacity.

7. The apparatus of claim 1 where in said computer readable instructions include instructions for actuating said indicator when said output temperature drop below a predetermined level.

8. The apparatus of claim 7 where in said computer readable instructions include instructions for actuating said indicator when said output temperature drop below 90° F.

9. The apparatus of claim 1 wherein said computer readable instructions include instructions for actuating said indicator to a first indication state when said output temperature his higher than 90° F., a second indication state when said output temperature is in the range of 70° F. and 90° F. and a third indication state when said output temperature is less than 70° F.

10. The apparatus of claim 1 including a power check actuator for executing said computer readable instructions of receiving power level information from said internal power supply.

11. The apparatus of claim 1 including a dissipation plate carried by said housing disposed between said heating element and said tubing to dissipate heat form said heating element across a portion of said tubing.

12. The apparatus of claim 1 wherein said heating element is a conductive thin film heating element and interlaced with said tubing.

13. The apparatus of claim 1 where in said computer readable instructions include instructions for determining whether an external power supply is connected and delivering power from said external power supply to said heating element if sand external power supply is connected and delivering power.

14. The apparatus of claim 1 wherein said external power supply is a BA-5590 battery.

15. The apparatus of claim 1 including an output connector stop included in said housing securing a portion of said fluid output connector in the interior of said housing and a portion of said fluid output connector external to said housing.

16. The apparatus of claim 1 including an input connector stop included in said housing securing a portion of said fluid input connector in the interior of said housing and a portion of said fluid input connector external to said housing.

17. The apparatus of claim 1 including a chassis carrying said internal power supply and said tubing wherein said chassis is removably attached to said housing.

18. The apparatus of claim 1 wherein said portable intravenous fluid heater weights less than 10oz.

19. The apparatus of claim 1 including an injured person receiving area for securing said housing to the injured person.

20. The apparatus of claim 1 wherein said computer readable instructions for increasing power to said heating element when said output temperature is below a predetermined temperature, include instructions for determining a duty cycle and applying power to said heating element until said duty cycle expires.

21. The apparatus of claim 1 wherein said computer readable instructions for increasing power delivered to said heating element if said input temperature is below a predestined temperature increases power to said heater element if said input temperature is below 50° F.

22. A portable intravenous fluid heater comprising:
a housing;
an internal power supply contained within said housing;
tubing having a tubing input connector external to said housing and a tubing output connector external to said housing;
a logic assembly carried by said housing having a processor and computer readable instructions;
a heating element connected to said logic assemble and adjacent to said tubing wherein said heating element is carried by said chassis and said heating element is removable connected to said logic assembly;
an output fluid heat sensor connected to said logic assembly disposed adjacent to a tubing output connector attached to said tubing output end for sensing the temperature of fluid flowing out of said tubing;
an external power terminal connected to said logic assembly for connecting an external power supply;
a power supply selection switch included in said logic assembly for switching from said internal power supply to a connected external power supply when a external power supply is connected and delivering power; and,
said computer readable instructions, when executed by said processor, perform the steps of receiving output temperature from said fluid output heat sensor, removing power from said heating element if said output temperature is above a predetermined temperature to reduce the temperature of fluid exiting said tubing and delivering power to said heating element when said output temperature is below a predetermined temperature.

23. The apparatus of claim 22 wherein said computer readable instructions include instructions for delivering power to said heating element when said output temperature drop below approximately 104° F. and discontinuing power to said heating element when said output temperature rises above approximately 104° F.

24. The apparatus of claim 22 wherein said heating element is a conductive thin film heating element and interlaced with said tubing.

25. The apparatus of claim 22 including a chassis removable attached to said housing and said logic assembly, said chassis carrying said internal power supply and said tubing.

26. The apparatus of claim 22 including a dissipation plate carried by said housing.

27. The apparatus of claim 22 wherein said portable intravenous fluid heater weights less than 10oz.

28. The apparatus of claim 22 including an indicator indicating operation status.

29. The apparatus of claim 28 wherein said computer readable instructions actuate said indicator when said output temperature drops below 90° F.

30. The apparatus of claim 28 where in said computer readable instructions include instructions for actuating said indicator to a first indication state when said output temperature is higher than 90° F., a second indication state when said output temperature is in the range of 70° F. and 90° F. and a third indication state when said output temperature is less than 70° F.

31. The apparatus of claim 28 wherein said computer readable instructions actuate said indicator when said internal power supply drops below 25% of said internal power supply's capacity.

32. The apparatus of claim 31 including a power check actuator for executing computer readable instructions for determining the remaining internal power supply capacity.

33. A portable intravenous fluid heater comprising:
a housing containing an internal power supply, tubing surrounding said internal power supply so that fluid flowing through said tubing receives auxiliary heat from said internal power supply, a logic assembly carried by said housing having a processor and connected to said internal power supply, and a heating element connected to said logic assemble wherein said logic assembly is removable attached to said housing so that said logic assembly can be removed from said housing and replaced with a second logic assembly;
an external battery terminal connected to said logic assembly for connecting an external battery;
a power supply selection switch included in said logic assembly for switching from said internal power supply to a connected external power supply when a external power supply is connected and delivering power; and,
a set of computer readable instructions included in said logic assembly that when executed by said processor performs the steps of receiving output temperature from an fluid output heat sensor, removing power from said heating element if said output temperature is above a predetermined temperature to reduce the temperature of fluid exiting said tubing and delivering power to said heating element for a determined duty cycle when said output temperature is below a predetermined temperature.

34. The apparatus of claim 33 wherein said heating element is a conductive thin film heating element interlaced with said tubing.

35. The apparatus of claim 33 including:
an input fluid sensor connected to said logic assembly and,
said computer readable instructions include instructions for receiving input temperature from said input fluid heat sensor, increasing power delivered to said heating element if said input temperature is below a predetermined temperature to heat fluid entering said tubing.

36. The apparatus of claim 33 including:
an internal clock included in said logic assembly for determining elapse time said heating element has been powered; and,
said computer readable instructions include instructions for receiving timing information from said internal clock, discontinuing power to said heating element after a predetermined period of time has elapsed.

37. The apparatus of claim 36 wherein said predetermined time is approximately 72 hours.

38. The apparatus of claim 33 including:
an electrical circuit defined by said logic assembly, said internal power supply and said heating element; and
a circuit breaker included in said electrical circuit for preventing current in excess of a predetermined amount to flow through said electrical circuit.

39. The apparatus of claim 33 including an electrical circuit defined by said logic assembly, said internal power supply, said heating element and a second heating element wherein said heating elements are electrically connected in parallel.

40. The apparatus of claim 33 including a chassis attached to said tubing and said internal power supply and removable attached to said housing so that said chassis can be removed from said housing and replaced with another chassis contained a second tubing and second intern power supply, said intern power supply being removable connected to said logic assembly.

41. The apparatus of claim 33 including fins included in said housing.

* * * * *